Figure 1:
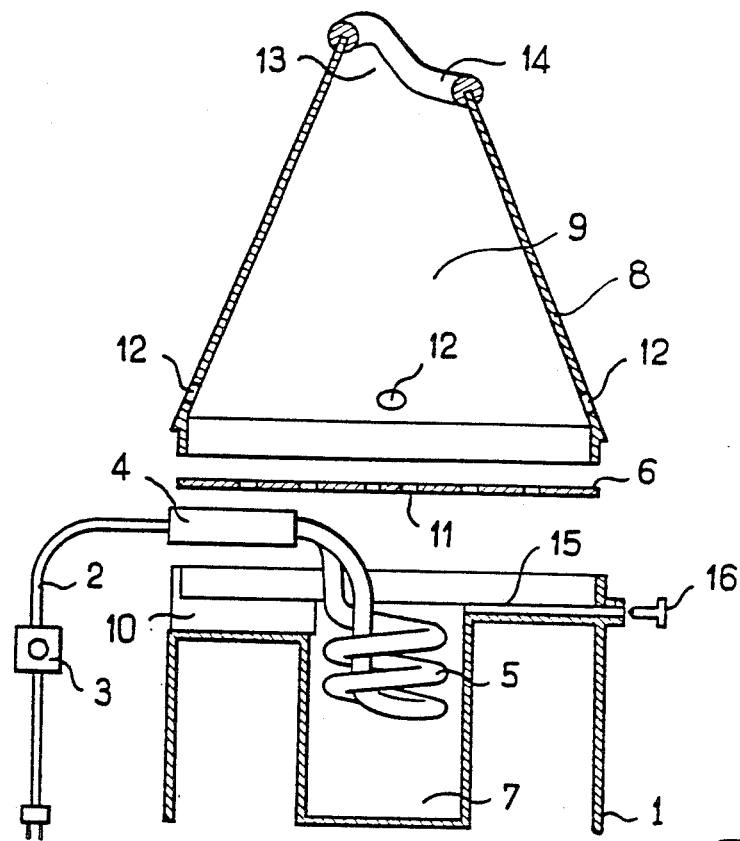

United States Patent [19]

Le Pabic

[11] Patent Number: 4,750,484
[45] Date of Patent: Jun. 14, 1988

[54] INHALER FOR CURING COLDS

[76] Inventor: Jean P. Le Pabic, 20, avenue des Acacias, 92500 Rueil Malmaison, France

[21] Appl. No.: 878,878
[22] PCT Filed: Sep. 19, 1985
[86] PCT No.: PCT/FR85/00255
§ 371 Date: Jul. 15, 1986
§ 102(e) Date: Jul. 15, 1986
[87] PCT Pub. No.: WO86/01732
PCT Pub. Date: Mar. 27, 1986

[30] Foreign Application Priority Data

Sep. 20, 1984 [FR] France .................. 84 14410

[51] Int. Cl.⁴ .................................... A61M 16/00
[52] U.S. Cl. ........................................ 128/203.27
[58] Field of Search .............. 128/203.16, 203.17, 128/203.26, 203.27, 204.17, 203.25

[56] References Cited

U.S. PATENT DOCUMENTS

| | | | |
|---|---|---|---|
| 513,804 | 1/1894 | Madden | 128/203.16 |
| 552,656 | 1/1896 | Anderson et al. | 128/203.16 |
| 892,441 | 7/1908 | Metzler | 128/203.16 |
| 2,023,324 | 12/1935 | Johnson et al. | 128/203.17 |
| 3,949,743 | 4/1976 | Shanbrom | 128/203.17 |

FOREIGN PATENT DOCUMENTS

| | | |
|---|---|---|
| 960469 | 4/1950 | France . |
| 1492214 | 8/1967 | France . |
| 526678 | 9/1940 | United Kingdom . |

*Primary Examiner*—William E. Kamm
*Assistant Examiner*—J. P. Lacyk
*Attorney, Agent, or Firm*—Young & Thompson

[57] ABSTRACT

An inhaler for curing colds applies the discoveries of the professor A. Lwoff. According to these discoveries, the patient must breathe during three sessions of 30 mn spaced apart two hours, hot air saturated in humidity, ideally at 43° C. A practical embodiment of the invention comprises an evaporation chamber (7) where water vapor is produced by boiling water. The necessary energy is produced by an immersible resistance heating element (5) and the delivery of vapor is adjustable with the aid of a power variator (3). This vapor penetrates into the mixing chamber (9) where it is mixed with air entering under the effect of the breathing of the patient. This heated air saturated with moisture is inhaled through an opening (13) where the patient introduces his nose.

8 Claims, 1 Drawing Sheet

INHALER FOR CURING COLDS

The present invention concerns an inhaler for curing colds applying recent discoveries of the professor A. LWOFF, discoveries which have been widely disseminated.

There already exist apparatus for curing colds applying these discoveries, but they require substantial means, particularly compressed air, systems for regulating the temperature and the degree of hydrometry and are therefore high in cost.

On the contrary, the present invention is of an extremely simple conception and therefore priced as a widely available object.

According to the discoveries of the professor A. LWOFF, the patient must breath warm air that is saturated with humidity for three sessions of 30 minutes, the sessions being spaced apart two hours. The temperature of this warm and humid air is situated ideally at 43° C. In effect, this temperature is largely sufficient that the treatment be efficient and it is undergone without inconvenience by the users.

To respond to these needs, a simple inhaler into which initially heated water has been poured is not adequate given that the duration of inhalation is very slight, on the one hand, and, on the other hand, the temperature of the respired humid air is too high from the outset which may result in scalding, and too low later on, which is inefficient.

There similarly exist inhalers containing a heating system, but these inhalers are not foreseen for such a use, given that the power furnished is not adapted to this usage and that they thus deliver a humid air the temperature of which is situated outside of the tolerances necessary for the treatment. On the other hand, they do not contain means for saturating the air with humidity.

On the contrary, the present invention is conceived in such a manner that the respired air is saturated in humidity on the one hand, and, on the other hand, the energy with which it is provided may be adjusted by the patient so as to obtain the desired temperature whatever may be his respiratory demand.

It comprises in effect, means intended to produce water vapor in an adjustable quantity by the user as a function of his respiratory demand. This water vapor is injected into a so-called mixing chamber (9) where it is mixed with air provided from the exterior under the breathing effort of the patient. Openings (12) situated in the lower part of this mixing chamber (9) are, in effect provided so as to permit the inlet of ambient air. Another opening (13) situated on the upper part of the said chamber (9) permits the patient to insert his nose therein and thus to breath therefrom the heated air that is saturated with humidity.

The following calculations will show that the air thus respired is saturated with humidity. There will be calculated, on the other hand, the power employed by the apparatus as well as the quantity of water consumed in the course of a session of 30 mn.

It is assumed that the ambient temperature is 20° C., which is generally the case of apartments heated in winter, and the quantity of water contained in the air is negligible in a first case.

At 43° C., the saturation vapor pressure of water is equal to 64.8 mm of mercury or 8.5% by volume.

The weight of a mole of water being 18 g, whereas that of air being 29 g, this gives the following weight percentages:

5.45% water, 94.55% air

The specific heat of air being equal to 1 J/g×°C., the quantity of heat necessary for elevating 94.55 g of air from 20° C. to 43° C. is equal to:

$$94.55 \times 1 \times (43-23) = 2175 \text{ j}$$

The specific heat of water vapor being equal to 1.9 J/g×°C., the quantity of heat furnished by lowering 5.45 g of water from 100° C. to 43° C. is equal to:

$$5.45 \times 1.9 \times (100-43) = 590 \text{ J}$$

This energy is less than that which is necessary for elevating 94.55 g of air from 20° C. to 43° C. The remainder must therefore necessarily come from the condensation of water, which assures the saturation.

Given that the missing energy is equal to: $2175 - 590 = 1585$ j and that the latent heat of vaporization of water at 43° C. is equal to 2410 J/g, it will be necessary to vaporize $1585/(1.9 \times 57 + 2410) = 0.63$ g supplementary water so as to obtain 100 g of air at 43° C. saturated with humidity.

The total quantity of water thus calculated is therefore equal to:

$$5.45 + 0.63 = 6.08 \text{ g.}$$

These results are now related to the volume of air respired by a user, which is situated essentially about 12 l/mn.

The mole of air having a volume of 22.4 l at 0° C. and a weight of 29 g, 94.55 g of air has a volume of:

$$94.55 \times (22.4/29) \times (1 + 43/273) = 84.5 \text{ l}$$

The same calculation related to water which has a molar weight of 18 g gives:

$$5.45 \times (22.4/18) \times (1 + 43/273) = 7.9 \text{ l}$$

There is thus obtained the total volume of humid air:

$$84.5 + 7.9 = 92.4 \text{ l}$$

The energy expended has been consumed by the vaporization at 100° C. of 6.08 g of water.

The latent heat of vaporization of the water at 100° C. being equal to 2245 J/g, this energy is equal to:

$$6.08 \times 2245 = 13,650 \text{ J}$$

The time necessary for the consumption of 92.4 l of air is equal to:

$$92 \times 60/12 = 460 \text{ s}$$

The power necessary is therefore:

$$13,650/460 = 30 \text{ W}$$

corresponding to a quantity of vapor produced per second equal to:

$$6.1/460 = 13 \times 10^{-3} \text{ g/s}$$

The total quantity of water consumed during a session of 30 mn is therefore equal to:

$$13 \times 10^{-3} \times 3 \times 60 = 23 \text{ g}$$

Naturally, the quantity of vapor produced must be adjusted as a function of the respiratory demand of the user. In a first embodiment, the vapor generator has a supplementary opening (15) toward the exterior, such that, this opening being adjustable by the user, it evacuates the excess produced vapor. Thus it is necessary to provide a power significantly greater than that which has been calculated previously so as to cover the case of any user whatsoever, for example 40 W.

The user thus proceeds to the adjustment such that the respired humid air be the hottest possible without provoking a burning sensation.

In a second embodiment, where the vapor generator is supplied in electric energy, the adjustment of the quantity of vapor produced is made by a power variator (3) interposed on the current supply cable. The user proceeds to the adjustment according to the same criterion as above.

In this case, it is possible to provide a maximum power much greater than that needed for the production of vapor, for example 300 W, so as considerably to shorten the heating duration of the water contained in the vapor generator. In effect, to heat 100 g of water from 20° C. to 100° C. with the aid of a power of 300 W there is needed:

$$100 \times (100-20) \times 4.18/300 = 111 \text{ s}$$

or 1 mn 51 s, whereas with a power of 40 W, there is needed:

$$100 \times (100-20) \times 4/18/40 = 836 \text{ s}$$

or 13 mn 56 s.

These adjustment possibilities of the one or the other embodiment cover, in addition, other factors which may influence the temperature of the air to be breathed. These are:

The temperature of the ambient air: The preceding calculations show that when the air is hottest, the quantity of vapor in excess, the condensation of which provokes the final heating, must be reduced.

The relative humidity of the ambient air: The more this humidity is elevated, the less the quantity of vapor to be produced will be.

The heat loss through the walls of the inhaler: In one embodiment where the vapor generator is not insulated against heat, these losses are not at all negligible and it is necessary to provide a supplementary power of about 20 W, which brings to 60 W the minimum power to be provided.

According to another characteristic of the invention, the volume of the mixing chamber (9) where the air-vapor mixing takes place prior to breathing, must be rather large and in particular greater than the volume of air corresponding to one breath.

If such were not the case, the fact that the passage of air across this chamber (9) is not regular, as it follows the respiratory rhythm of the user, would provoke an irregular mixture of the air and the vapor resulting in disadvantageous temperature variations. On the contrary, if the volume of the said chamber (9) is sufficient, for example 1 l, at each breath a portion of the heated and humidified air is replaced by the cold and dry air which is heated and is saturated during the expiration.

According to a preferred embodiment, the vapor generator is constituted by a chamber called the evaporation chamber (7) of reduced volume, for example 0.1 l intended to receive water to be evaporated and containing an immersible resistance heating element (5) connected to a source of electricity.

This chamber (7) is closed at its upper extremity by a cover (6) having openings (11) through which the vapor passes into the mixing chamber (9).

Given the small volume of the evaporation chamber (7) and the fact that this latter must be located at the lower portion of the inhaler, there could follow problems of stability when this latter is posed on a horizontal surface.

That is why this chamber (7) is fixed in a cylinder of greater diameter assuring a good stability and on which comes to fit simultaneously the cover (6) of the evaporation chamber (7) and the cover (8) of the mixing chamber (9).

This cover (8) is constituted by a revolution cone positioned with its base lowermost and at the upper extremity of which is found the opening (13) into which the patient introduces his nose. So as simultaneously to increase the tightness of the seal and the comfort of use, the edges of the opening are provided with a padding (14).

On the lower part are provided the inlet holes (12) for ambient air.

The following description, in connection with the accompanying drawings, given purely by way of non-limiting example, will permit understanding of how the invention may be realized.

The drawings show:

In FIG. 1: the different parts of the inhaler, namely:

A section along a vertical plane of the base (1) of the inhaler.

The assembly of the electric cord (2), power variator (3) provided in one embodiment, collar (4) and resistance heating element (5).

A section along a vertical plane of the cover (6) of the evaporation chamber (7).

A section along a vertical plane of the cover (8) of the mixing chamber (9).

Figure 2:
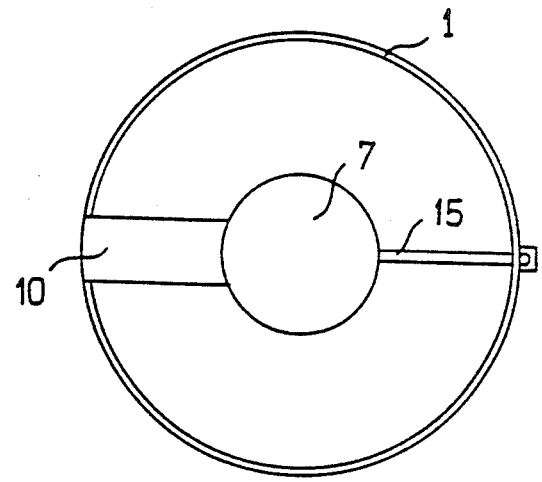

In FIG. 2: a view from above of the base (1). The collar (4) and the resistance heating element (5) come to be placed in the conduit (10) of the base (1) of the inhaler, which results in the positioning of the resistance heating element (5) in the evaporation chamber (7). The user pours the water intended for vapor production therein.

These dimensions, equal to 2.5 cm for the interior radius and 6 cm for the height, mean that its capacity is about 0.1 l. The cover (6) of the evaportion chamber (7) is placed in the interior of the walls of the base (1) above this chamber (7). It is maintained there by the cover (8) of the mixing chamber (9) which is fitted in the interior of the base (1) and fixes the assembly.

Holes (11) in the cover (6) of the evaporation chamber (7) allow the vapor to be injected into the mixing chamber (9).

Holes (12) situated at the bottom of the cover (8) of the mixing chamber (9) allow the exterior air to penetrate therein at the time of breathing by the user. This latter places his nose in the upper opening (13) provided with a padding (14).

According to an embodiment, a conduit (15) places the evaporation chamber (7) and the exterior in communication. This conduit may be more or less sealed by acting on the screw (16).

The inhaler according to the invention is particularly intended for curing colds.

I claim:

1. Inhaler for curing colds, comprising means adapted to receive the nose of a user, means for generating water vapor, and a mixing chamber interconnecting said water vapor-generating and nose-receiving means, said mixing chamber comprising means introducing ambient air into said chamber responsive to each inhalation by a said user, whereby a mixing of water vapor generated by said water vapor-generating means and ambient air is effected in said mixing chamber at each inhalation by said user, said mixing chamber being downwardly limited by a cover covering said water vapor-generating means and upwardly limited by a conical cover having at its base said ambient air-introducing means in the from of a plurality of holes in said conical cover.

2. Inhaler according to claim 1, wherein said cover downwardly limiting said mixing chamber comprises a plurality of water vapor discharge holes permitting passage of water vapor from said water vapor-generating means to said mixing chamber.

3. Inhaler according to claim 1, wherein said water vapor-generating means comprises a submersible electrical heating element.

4. Inhaler according to claim 1, wherein said water vapor-generating means comprises means for adjusting delivery of water vapor to said mixing chamber.

5. Inhaler according to claim 1, wherein said nose-receiving means comprises an opening effected in the top of said conical cover, said opening being provided with a padding ensuring comfort of said user and an air-tight seal between said user's nose and said opening.

6. Inhaler according to claim 1, wherein said mixing chamber has a volume greater than the volume of air which can be inhaled by a said user in a single breath.

7. Inhaler according to claim 3, wherein said submersible electrical heating element comprises a power variator for adjusting delivery of water vapor to said mixing chamber.

8. Inhaler for curing colds, comprising means adapted to receive the nose of a user, means for generating water vapor, and a mixing chamber interconnecting said water vapor-generating and nose-receiving means, said mixing chamber comprising means introducing ambient air into said chamber responsive to each inhalation by a said user, whereby a mixing of water vapor generated by said water vapor-generating means and ambient air is effected in said mixing chamber at each inhalation by said user, said vapor-generating means comprising a conduit for evacuating a portion of the water vapor produced in said vapor-generating means into the atmosphere, said conduit having an adjustable cross-sectional area.

* * * * *